United States Patent [19]

Ohno et al.

[11] Patent Number: 5,892,134
[45] Date of Patent: Apr. 6, 1999

[54] METHOD FOR PRODUCING PERFLUOROCARBON

[75] Inventors: Hiromoto Ohno; Tetsuo Nakajo; Toshio Ohi; Tatsuharu Arai, all of Kanagawa, Japan

[73] Assignee: Showa Denko K.K., Tokyo, Japan

[21] Appl. No.: 1,917

[22] Filed: Dec. 31, 1997

[30] Foreign Application Priority Data

Jun. 18, 1997 [JP] Japan ..................................... 9-161397

[51] Int. Cl.$^6$ .................................................. C07C 19/08
[52] U.S. Cl. ................................................................ 570/123
[58] Field of Search ............................................. 570/123

[56] References Cited

U.S. PATENT DOCUMENTS

| | | | |
|---|---|---|---|
| 4,377,715 | 3/1983 | Nychka et al. ........................... | 570/123 |
| 5,406,008 | 4/1995 | Sievert ..................................... | 570/123 |
| 5,434,319 | 7/1995 | Herkelmann et al. ................... | 570/123 |
| 5,710,351 | 1/1998 | Ohno et al. .............................. | 570/123 |

*Primary Examiner*—Alan Siegel
*Attorney, Agent, or Firm*—Sughrue, Mion, Zinn, Macpeak & Seas, PLLC

[57] ABSTRACT

A production method of perfluorocarbon comprising a main reaction step of making a hydrofluorocarbon and fluorine gas of raw materials react in vapor phase with each other to obtain a reaction product gas containing a perfluorocarbon and residual fluorine gas, and a fluorine gas removing step of making the reaction product gas effluent from the main reaction step contact a hydrofluorocarbon having a chemical equivalent not less than 1.1 mol times a chemical equivalent of the fluorine gas contained in the reaction product gas, thereby removing the fluorine gas.

5 Claims, No Drawings

METHOD FOR PRODUCING PERFLUOROCARBON

BACKGROUND OF THE INVENTION

1. Field of the Invention

The present invention relates to a method for producing a perfluorocarbon by reaction between a hydrofluorocarbon and fluorine gas and, more particularly, to a production method of perfluorocarbon for advantageously removing residual fluorine gas existing in a gas of reaction product.

2. Related Background Art

A method for producing a perfluorocarbon by vapor phase reaction between a hydrofluorocarbon and fluorine gas at an elevated temperature is known in general. In order to efficiently produce the perfluorocarbon by this reaction, it is necessary to use an excessive mol of fluorine gas over the hydrofluorocarbon of raw material. Thus, the reaction product gas effluent from this reaction step contains the residual fluorine gas. A variety of proposals have been presented heretofore on methods for removing the fluorine gas from this reaction product gas.

For example, the known methods include a method for burning the fluorine gas in the reaction product gas together with a hydrocarbon and washing the product of hydrogen fluoride with an alkali (Nobuatsu Watanabe, "Fluorine Gas Chemistry and Industry I," p. 42, 1973), a method for making the fluorine gas in the reaction product gas react with an inorganic oxide such as alumina or soda lime to convert it to fluorides, a method for making the fluorine gas react with superheated steam to remove it (for example, Mary Howe-Grant, Editor "Fluorine Chemistry: A Comprehensive Treatment" 1995, p. 20), and so on.

SUMMARY OF THE INVENTION

In the aforementioned method for burning the fluorine gas together with the hydrocarbon, however, the reaction proceeds violently and the reaction control is thus difficult. Use of excessive hydrocarbon for complete removal of fluorine gas will complicate the composition of product and leave big difficulties in subsequent separation and purification. In the method for making the fluorine gas react with the inorganic oxide such as alumina or soda lime, since this reaction produces water, a dehydration step is necessitated as a post step, which will complicate the production process and pose the problem of corrosion of reaction system. In the method using superheated steam, the reaction control is also difficult and this method also necessitates the dehydration step as a post step. Further, high-grade corrosion-resistant materials have to be used for prevention of corrosion of reaction system, so that this method also imposes great loads on the facilities and process.

In either of the conventional methods described above, the expensive fluorine gas is not recovered and is discharged in the form of fluorides. Therefore, the conventional methods had the problems in economical and environmental aspects and were not always advantageous methods. An object of the present invention is, therefore, to provide a cheap and simple method for removing the fluorine gas from the reaction product gas while effectively utilizing the residual fluorine gas.

The inventors found that the above problems were solved by a main reaction step for making a hydrofluorocarbon and fluorine gas of raw materials react in vapor phase with each other and a fluorine gas removing step for making a reaction product gas effluent from this main reaction step contact a hydrofluorocarbon having a chemical equivalent not less than 1.1 mol times a chemical equivalent of the fluorine gas contained in the reaction product gas.

The present invention thus provides a production method of perfluorocarbon comprising a main reaction step of making a hydrofluorocarbon and fluorine gas of raw materials react in vapor phase with each other to obtain a reaction product gas containing a perfluorocarbon and residual fluorine gas, and a fluorine gas removing step of making the reaction product gas effluent from the main reaction step contact a hydrofluorocarbon having a chemical equivalent not less than 1.1 mol times a chemical equivalent of the fluorine gas contained in the reaction product gas, thereby removing the fluorine gas.

In the aforementioned main reaction step, the hydrofluorocarbon of raw material is preferably an aliphatic compound the carbon number of which is not more than 6.

In the aforementioned fluorine gas removing step, the hydrofluorocarbon made to contact the reaction product gas is preferably a hydrofluorocarbon that can produce the aimed perfluorocarbon when reacting with the fluorine gas.

In the aforementioned fluorine gas removing step, a treatment temperature is preferably equal to or higher than a reaction temperature in the main reaction step.

In the aforementioned fluorine gas removing step, hydrogen fluoride gas is preferably made present as a diluent gas.

DESCRIPTION OF THE PREFERRED EMBODIMENTS

The production method of perfluorocarbon according to the present invention fundamentally comprises the main reaction step of making the hydrofluorocarbon and fluorine gas of raw materials react in vapor phase with each other, and the fluorine gas removing step of removing the residual fluorine gas contained in the reaction product gas effluent from this main reaction step.

The aforementioned main reaction step is a step for making the hydrofluorocarbon and fluorine gas react in vapor phase at an elevated temperature to convert them to a perfluorocarbon and hydrogen fluoride. In this reaction, generally, an excessive mol of fluorine gas is used over the hydrofluorocarbon of raw material in order to increase reaction efficiency. Therefore, the reaction product gas effluent from the main reaction step contains residual fluorine gas in addition to the perfluorocarbon and hydrogen fluoride. According to the present invention, the fluorine gas contained in the reaction product gas effluent from the main reaction step is removed in the fluorine gas removing step by making it contact and react with the hydrofluorocarbon having a chemical equivalent not less than 1.1 mol times a chemical equivalent of the fluorine gas. This reaction converts the fluorine gas to the perfluorocarbon (or hydrofluorocarbons) and hydrogen fluoride. The perfluorocarbon produced in this step is a part of the final product and the hydrofluorocarbons can be circulated to the main reaction step. Hence, the residual fluorine gas can be effectively removed from the reaction product gas while being effectively utilized, without being converted to unwanted fluorides or the like to be discharged.

The present invention is suitably applicable to production of aliphatic perfluorocarbons the carbon numbers of which are not more than 6. Namely, the hydrofluorocarbon supplied as a raw material in the main reaction step is preferably an aliphatic compound the carbon number of which is not more than 6. For producing a perfluorocarbon by reaction between fluorine gas and a hydrofluorocarbon with the carbon number exceeding 6, the main reaction step and fluorine gas removing step both have to be carried out under severer reaction conditions, for example, at extremely high temperatures, which could partially decompose the perfluorocarbon produced so as to cause a loss of the final product. From this point, the present invention is particularly suitable for production of perfluorocarbons the carbon numbers of which are not more than 6, more preferably, not more than 4.

The hydrofluorocarbon made to contact the reaction product gas in the aforementioned fluorine gas removing step is preferably the same as the hydrofluorocarbon supplied as a raw material in the main reaction step or a hydrofluorocarbon that can react with the fluorine gas to produce the same perfluorocarbon. In this method, the perfluorocarbon produced by the reaction with the fluorine gas in the fluorine gas removing step is the same as that produced in the main reaction step. Therefore, the composition of product gas is simple and the steps of separation and purification seem likely to be simplified.

Even in the case where a mixture of two or more perfluorocarbons is produced, the residual fluorine gas can be advantageously removed by using a hydrofluorocarbon that can produce at least one of the perfluorocarbons in the mixture, in the fluorine gas removing step.

In the fluorine gas removing step the treatment temperature is preferably equal to or higher than the reaction temperature in the main reaction step. If the treatment temperature in the fluorine gas removing step is lower than the reaction temperature in the main reaction step, it will tend to be rather difficult to reduce a concentration of fluorine gas in the product gas down to a practically sufficient level (for example, not more than 1 ppm by weight). In practice, the treatment temperature in the fluorine gas removing step is preferably higher than the reaction temperature in the main reaction step and more preferably 200° to 600° C. higher than the reaction temperature in the main reaction step.

In general, reaction occurs violently between hydrofluorocarbons and fluorine gas under a heated condition and in a high concentration of fluorine gas, so that control of reaction tends to be rather difficult. Therefore, the reaction is preferably made to proceed in a system diluted with an inert gas. Hydrogen fluoride can be used as at least a part of this diluent gas. Since the hydrogen fluoride is a substance originally produced by the reaction between the hydrofluorocarbon and fluorine gas, use of this advantageously eliminates the need for an extra diluent gas separation step in the subsequent purification step.

The diluent gas is preferably present both in the main reaction step and in the fluorine gas removing step. When hydrogen fluoride is used as a diluent gas in the main reaction step and is introduced into the fluorine gas removing step without being removed from the reaction product gas, the hydrogen fluoride also functions as a diluent gas in the fluorine gas removing step, so that a new diluent gas does not have to be added to the fluorine gas removing step.

The constituent elements of the present invention will be described below in further detail.

The perfluorocarbon as a produced object in the present invention is an aliphatic compound composed of only carbon and fluorine atoms, which is preferably a compound the carbon number of which is 1–6 and more preferably a compound the carbon number of which is 1–4. Examples of perfluorocarbons suitably produced by the method of the present invention are tetrafluoromethane ($CF_4$), hexafluoroethane ($CF_3$—$CF_3$), tetrafluoroethene ($CF_2$=$CF_2$), octafluoropropane ($C_3F_8$), hexafluoropropene ($CF_2$=$CF$—$CF_3$), decafluorobutane ($C_4F_{10}$), octafluorocyclobutane (cyclic (—$CF_2$—$CF_2$—)$_2$), octafluorobutene-1 ($CF_2$=$CF$—$CF_2$—$CF_3$), octafluorobutene-2 ($CF_3$—$CF$=$CF$—$CF_3$), and so on. These may be single compounds or mixtures. They may be mixtures of perfluorocarbon and hydrofluorocarbon if necessary.

The hydrofluorocarbon used as a raw material of the main reaction step together with fluorine gas is an aliphatic compound composed of carbon, hydrogen, and fluorine atoms and having a carbon framework corresponding to that of the aforementioned perfluorocarbon being the produced object. Accordingly, the hydrofluorocarbon is preferably an aliphatic compound the carbon number of which is 1–6 and more preferably an aliphatic compound the carbon number of which is 1–4. Examples of such compounds include fluoromethane ($CH_3F$), difluoromethane ($CH_2F_2$), trifluoromethane ($CHF_3$), fluoroethane ($CH_3$—$CH_2F$), difluoroethane, trifluoroethane, tetrafluoroethane, pentafluoroethane ($CF_3$—$CHF_2$), fluoropropane, difluoropropane, trifluoropropane, tetrafluoropropane, pentafluoropropane, hexafluoropropane, heptafluoropropane, and so on. In general, they are compounds represented by $C_xF_yH_z$ where x is 1–6 and y and z are each within the range of 1 to (2x+1), and preferably non-cyclic saturated compounds wherein y+z=(2x+2), or cyclic saturated or unsaturated compounds wherein y+z=2x. These compounds may be used singly or in the form of mixtures of two or more.

The above hydrofluorocarbon is preferably one substantially containing no such impurities as chlorine-containing compounds, e.g. pentafluorochloroethane or trifluorochloromethane, or bromine-containing compounds, e.g. trifluorobromomethane. Since these impurities cannot be removed in the fluorine gas removing step, the subsequent separation and purification steps tend to become rather difficult. A permissible content of these chlorine-containing impurities is preferably not more than 2 mol% in the raw-material hydrofluorocarbon, more preferably not more than 1 mol%, and particularly preferably not more than 0.5 mol%; a permissible content of the bromine-containing compounds is preferably not more than 0.1 mol%, more preferably not more than 0.01 mol%, and particularly preferably not more than 0.002 mol%.

The fluorine gas used as a raw material is generally obtained industrially by electrolysis of hydrogen fluoride. As the raw material of the present invention, the fluorine gas resulting from electrolysis may be used as it is, or fluorine gas filled in a cylinder or fluorine gas diluted with an inert gas may also be used.

In the main reaction step of the present invention the method for producing the perfluorocarbon by the reaction between the hydrofluorocarbon and fluorine gas at the elevated temperature is commonly known. On the occasion of reaction the supply ratio of the hydrofluorocarbon and fluorine gas can be basically determined arbitrarily, but, also considering the subsequent separation step and decontamination step, it is advantageous to supply the fluorine gas by at least one equivalent, preferably an excess equivalent, per equivalent of hydrogen of the hydrofluorocarbon under controllable reaction conditions. Under the conditions of excessive supply of fluorine gas, almost 100% of the hydrofluorocarbon can be converted to the perfluorocarbon, but, at the same time, it is a matter of course that residual fluorine gas is also contained in the reaction product gas.

For advantageously removing this residual fluorine gas, the present invention involves the fluorine gas removing step of making the reaction product gas contact the hydrofluorocarbon. The hydrofluorocarbon used in this step (hereinafter referred to as "removing-step hydrofluorocarbon") is basically preferably the same as the hydrofluorocarbon used as a raw material in the aforementioned main reaction step (hereinafter referred to as "raw-material hydrofluorocarbon"). It is also possible to use a hydrofluorocarbon different from the raw-material hydrofluorocarbon, but, in most cases, it would be the cause of changing the optimum reaction conditions and tend to raise the inconvenience of complexing the subsequent separation and purification steps, or the like. However, a different hydrofluorocarbon may be used for removal if it has higher reactivity than the raw-material hydrofluorocarbon and can be readily separated in the purification step. Further, a removing-step hydrofluorocarbon different from the raw-material hydrofluorocarbon can be used without any specific problems if it produces the same perfluorocarbon as the raw-material hydrofluorocarbon in reaction with fluorine gas, for example, as in a case where the raw-material hydrofluorocarbon is trifluoromethane and the removing-step hydrofluorocarbon is difluoromethane.

In the fluorine gas removing step, a supply amount of the removing-step hydrofluorocarbon to the reaction product gas from the main reaction step is not less than 1.1 mol times a chemical equivalent of the fluorine gas contained in this reaction product gas. By supplying the hydrofluorocarbon substantially exceeding the chemical equivalent, a concentration of fluorine gas in recovered gas can be decreased down to the practical level, for example, of not more than 1 ppm by weight. In practice, the supply amount of the removing-step hydrofluorocarbon to the fluorine gas contained in the reaction product gas is preferably 1.1 mol times to 100 mol times the chemical equivalent and more preferably 1.5 mol times to 30 mol times the chemical equivalent. Below 1.1 mol times, the reaction will not proceed sufficiently, so that the concentration of fluorine gas in the recovered gas cannot be lowered to the practical level. Use of the hydrofluorocarbon over 100 mol times will result in recognizing no enhancement of effect and thus tend to be disadvantageous from the economical aspect.

The fluorine gas removing step can be carried out by use of a reactor of the vapor phase flow system. This reactor is constructed of a stable material against the components, temperatures, and pressures of system and may be either of a single pipe type or of a multipipe type as long as it permits heating and heat-eliminating control. The material can be a pipe of SUS316 if the treatment temperature is relatively low and the throughput is small, but the material is normally selected preferably from inconel, Monel (trade name), Hastelloy C (trade name), nickel, and so on.

A preferred setting value of the treatment temperature in the fluorine gas removing step is selected depending upon the composition of the reaction product gas from the main reaction step and upon the type and amount of the removing-step hydrofluorocarbon. For example, when the raw-material and removing-step hydrofluorocarbons both are trifluoroethane ($CF_3$—$CH_3$) with high reactivity, the purpose can be achieved even at relatively low temperatures, for example, at about 200° C. For another example, when pentafluoroethane with relatively low reactivity is used, high-temperature conditions, for example, 350° C. or higher, are preferred.

However, if the treatment temperature in the fluorine gas removing step is, for example, over 600° C., it will tend to raise the inconvenience of partially decomposing the perfluorocarbon produced. From this viewpoint, the treatment temperature in the fluorine gas removing step is preferably in the range of 200° C. to 600° C. inclusive.

When the concentration of the fluorine gas in the reaction product gas in the main reaction process is high and when it is made to contact the hydrofluorocarbon at the elevated temperature, the reaction is too violent, so that the control tends to be rather difficult. For solving this problem, an inert diluent gas is used suitably, and hydrogen fluoride can be advantageously used as this diluent gas. Namely, since the hydrogen fluoride is produced by the reaction between the raw-material hydrofluorocarbon and fluorine gas in the main reaction step, it can be used as the diluent gas in the fluorine gas removing step without having to be separated. It can also be contemplated that the hydrogen fluoride separated in the subsequent separation and purification steps of perfluorocarbon is circulated as a diluent gas of the main reaction step or the fluorine gas removing step. This method permits the diluent gas to exist in a necessary amount for control in the system without adding a new diluent gas.

There is no specific limitation on the treatment pressure in the fluorine gas removing step, but it is generally in the range of 0 to 3 MPa inclusive. Particularly, the operation is carried out preferably in the range of the atmospheric pressure to 0.5 MPa in terms of safety and costs for facilities and operation.

EXAMPLES

Examples of the present invention will be described below, but it is noted that the present invention is by no means intended to be limited to these examples. In the below examples % and ppm all indicate mole proportions.

Production of Tetrafluoromethane From Difluoromethane (Example 1)

Main reaction step: Difluoromethane ($CH_2F_2$, "Ecoloace 32" available from Showa Denko K. K.) was made to react with fluorine gas at 280° C., thereby obtaining the reaction product gas.

This reaction product gas contained 99.1% tetrafluoromethane ($CF_4$) on an organic basis. When measured by the potassium iodide method, the concentration of fluorine gas was 0.56%.

Fluorine gas removing step: With the reactor of inconel 600 having the inside diameter of 20.6 mm$\phi$ and the length 500 mm (of the electrothermal type, the inside of which had been processed by a passivation treatment at 600° C. with fluorine gas), the treatment temperature was set to 330° C., and the reaction product gas was introduced at 100 NL/h and difluoromethane for removal of fluorine gas at 2.47 NL/h into the reactor, thereby achieving concurrent flow contact thereof. The supply amount of this removing-step difluoromethane was 4.4 mol times to the fluorine gas in the reaction product gas. A concentration of fluorine gas in recovered gas after three hours was 0.4 ppm.

(Example 2, Example 3)

The main reaction step and fluorine gas removing step in Example 2 and Example 3 were carried out in the same manner as in Example 1 except that the treatment temperature in the fluorine gas removing step was changed as described below. Concentrations of fluorine gas in recovered gas obtained are also shown below.

| Example | Reaction temperature | Concentration of fluorine gas |
|---|---|---|
| 2 | 280° C. | 0.11% |
| 3 | 450° C. | not more than 0.1 ppm |

It is seen from the results of Example 1 to Example 3 that in production of tetrafluoromethane, the concentrations of fluorine gas can be effectively reduced by using the same hydrofluorocarbon in the fluorine gas removing step as the raw material. In this case, even the relatively low temperature (280° C. in Example 2) approximately equal to that in the main reaction step was also effective for removal of fluorine gas, but, by further increasing the reaction temperature, the concentration of fluorine gas was able to be decreased down to the practically sufficient level (for example, not more than 1 ppm).

Production of Tetrafluoromethane From Trifluoromethane (Example 4, Example 5)

Main reaction step: Trifluoromethane ($CHF_3$) was made to react with fluorine gas at 400° C., thereby obtaining the reaction product gas.

This reaction product gas contained 98.89% tetrafluoromethane ($CF_4$) on an organic basis. When measured by the potassium iodide method, the concentration of fluorine gas was 0.61%.

Fluorine gas removing step: With the same reactor as in Example 1, the reaction temperature was set to 480° C., and the above reaction product gas was introduced at 60 NL/h and trifluoromethane ($CHF_3$) for removal of fluorine gas at different supply rates described below, thus achieving concurrent flow contact thereof. Concentrations of fluorine gas in recovered gas after three hours are shown below.

| Example | Supply rate of $CHF_3$ | Concentration of fluorine gas |
|---|---|---|
| 4 | 2.78 NL/h | 57 ppm |
| 5 | 6.10 NL/h | not more than 0.1 ppm |

It is seen from the results of Example 4 and Example 5 that in production of tetrafluoromethane, trifluoromethane, though having lower reactivity than difluoromethane, can decrease the concentrations of fluorine gas down to the sufficiently practical level by selecting the conditions properly.

Production of Tetrafluoromethane Using Different Hydrofluorocarbons (Example 6)

Main reaction step: Trifluoromethane ($CHF_3$) was made to react with fluorine gas at 400° C., thereby obtaining the reaction product gas.

This reaction product gas contained 98.89% tetrafluoromethane ($CF_4$) on an organic basis. When measured by the potassium iodide method, the concentration of fluorine gas was 0.61%.

Fluorine gas removing step: The recovered gas was obtained in the same manner as in Example 5 except that difluoromethane was used instead of trifluoromethane. A concentration of fluorine gas in the recovered gas after three hours was not more than 0.1 ppm.

It is seen from the result of Example 6 that in production of tetrafluoromethane the concentration of fluorine gas can also be decreased down to the sufficiently practical level by using the hydrofluorocarbon different from the raw material, for removal of fluorine gas.

Production of Hexafluoroethane From Tetrafluoroethane (Example 7 to Example 9)

Main reaction step: Tetrafluoroethane ($CH_2F$—$CF_3$, "Ecoloace 134a" available from Showa Denko K. K.) was made to react with fluorine gas at 250° C., thereby obtaining the reaction product gas.

This reaction product gas contained 95.2% hexafluoroethane ($CF_3$—$CF_3$) on an organic basis. A conversion ratio of tetrafluoroethane was 100%. The reaction product gas contained 0.20% fluorine gas when measured by the potassium iodide method.

Fluorine gas removing step: With the same reactor as in Example 1, the same tetrafluoroethane as the raw material was used for removal of fluorine gas and was made to contact the reaction gas product under the below conditions, thus obtaining recovered gas. Concentrations of fluorine gas in the recovered gas after three hours are shown below.

| Example | Reaction temperature | Rate of reaction product gas | Rate of $CH_2F$—$CF_3$ for removal | Concentration of fluorine gas |
|---|---|---|---|---|
| 7 | 300° C. | 100 NL/h | 0.67 NL/h | 10 ppm |
| 8 | 400° C. | 60 NL/h | 0.28 NL/h | 1.3 ppm |
| 9 | 450° C. | 60 NL/h | 0.27 NL/h | 0.5 ppm |

It is seen from the results of Example 7 to Example 9 that in production of hexafluoroethane the concentrations of fluorine gas were also able to be decreased down to the sufficiently practical level by selecting the conditions properly.

Production of Octafluorocyclobutane From Hexafluorocyclobutane (Example 10)

Main reaction step: Hexafluorocyclobutane was made to react with fluorine gas at 375° C., thereby obtaining the reaction product gas.

This reaction product gas contained 0.18% fluorine gas.

Fluorine gas removing step: With the same reactor as in Example 1, tetrafluoroethane was used for removal of fluorine gas and was made to contact the reaction product gas at 400° C., thereby obtaining recovered gas. A concentration of fluorine gas in the recovered gas was decreased down to 35 ppm.

Production of Mixed Perfluorocarbons (Example 11)

Main reaction step: In a first reaction zone trifluoromethane was made to react with fluorine gas at 350° C. under presence of a diluent gas of hydrogen fluoride; and subsequently, in a second reaction zone this reaction product gas was mixed with raw-material tetrafluoroethane (containing 11 ppm $CHF_2$—$CHF_2$ and the rest $CH_2F$—$CF_3$) and additional fluorine gas to undergo reaction at 300° C., thereby obtaining a mixed reaction product gas of tetrafluoromethane and hexafluoroethane.

This mixed reaction product gas contained 0.15% fluorine gas.

Fluorine gas removing step: With the same reactor as in Example 1, the above raw-material tetrafluoroethane was used for removal of fluorine gas and was made to contact the above mixed reaction product gas under ordinary pressure and at 400° C., thereby obtaining recovered gas. A concentration of fluorine gas in the recovered gas was decreased down to not more than 0.1 ppm.

(Example 12)

The recovered gas was obtained in the same manner as in Example 11 except that the internal pressure of the reactor in the fluorine gas removing step was increased to 0.3 MPa. The concentration of fluorine gas in the recovered gas was not more than 0.1 ppm. It is seen from this result that the same removing effect of fluorine gas can be achieved even by increasing the internal pressure in the reactor in the fluorine gas removing step.

Since the production method of perfluorocarbon according to the present invention involves the fluorine gas removing step of making the reaction product gas effluent from the main reaction step contact the hydrofluorocarbon having a chemical equivalent not less than 1.1 mol times a chemical equivalent of the fluorine gas contained in the reaction product gas, the perfluorocarbon substantially containing no fluorine gas can be produced cheaply and easily, without necessitating an additional dehydration step or the like, without discharging the expensive fluorine gas in the form of fluorides or the like, and with effectively utilizing the residual fluorine gas.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method of producing a perfluorocarbon comprising a main reaction step wherein a hydrofluorocarbon and fluorine gas react in vapor phase with each other to obtain a reaction product gas containing a perfluorocarbon and residual fluorine gas, and a fluorine gas removing step wherein the reaction product gas effluent from the main reaction step contact a hydrofluorocarbon having a chemical equivalent not less than 1.1 mol times a chemical equivalent of the fluorine gas contained in the reaction product gas, thereby removing the fluorine gas.

2. A method of producing a perfluorocarbon according to claim 1, wherein, in said main reaction step, the hydrofluorocarbon is an aliphatic compound the carbon number of which is not more than 6.

3. A method of producing a perfluorocarbon according to claim 1, wherein, in said fluorine gas removing step, the hydrofluorocarbon made to contact the reaction product gas is a hydrofluorocarbon that can produce the desired perfluorocarbon when reacting with the fluorine gas.

4. A method of producing a perfluorocarbon according to claim 1, wherein, in said fluorine gas removing step, the treatment temperature is equal to or higher than the reaction temperature in the main reaction step.

5. A method of producing a perfluorocarbon according to claim 1, wherein, in said fluorine gas removing step, hydrogen fluoride gas is added as a diluent gas.

* * * * *